United States Patent [19]

Deryagina et al.

[11] 4,035,424

[45] July 12, 1977

[54] METHOD OF PREPARING SYMMETRICAL DIARYLSULPHIDES

[76] Inventors: Eleonora Nikolaevna Deryagina, ulitsa Lermontova, 313a, kv. 32;
Mikhail Grigorievich Voronkov, ulitsa Lermontova, 315, kv. 32;
Anatoly Samuilovich Nakhmanovich, ulitsa Rossiiskaya, 6, kv. 26;
Ljudmila Gerasimovna Klochkova, ulitsa Lermontova, 100, kv. 12, all of Irkutsk, U.S.S.R.

[21] Appl. No.: 565,098

[22] Filed: Apr. 4, 1975

[51] Int. Cl.$^2$ .................................... C07C 148/00
[52] U.S. Cl. .......................................... 260/609 E
[58] Field of Search ............................... 260/609 A

[56] References Cited

U.S. PATENT DOCUMENTS

| | | | |
|---|---|---|---|
| 1,993,287 | 3/1935 | Seaman | 260/609 A |
| 2,035,121 | 3/1936 | Frolich | 260/609 A |
| 2,066,189 | 12/1936 | Seaman | 260/609 A |

OTHER PUBLICATIONS

Limido, et al.; Chem. Abst. vol. 44 (1950) pp. 3877.

*Primary Examiner*—Delbert R. Phillips
*Attorney, Agent, or Firm*—Fleit & Jacobson

[57] ABSTRACT

This invention provides a method of preparing a symmetrical diarylsulphide which consists of passing an aromatic thiol, such as thiophenol, 4-thiocresol, and 1-thionaphthol, through a gas inert to said thiol, such as nitrogen, at a temperature of about from 500° C to 600° C to produce a symmetrical diarylsulphide, such as diphenylsulphide, di(4-tolyl) sulphide, and di(1-naphthyl) sulphide, and isolating said diarylsulphide.

7 Claims, No Drawings

METHOD OF PREPARING SYMMETRICAL DIARYLSULPHIDES

This invention relates to a method of preparing symmetrical diarylsulphides used in various branches of the national economy as additives to oils, monomers, intermediate products of organic synthesis, insecticides, growth stimulants, plasicizing agents, etc. Diphenylsulphide can be used also as a high-boiling inert solvent.

Known in the prior art are methods for preparing diarylsulphides which involve reacting thiophenolates of heavy metals with aryl halides and aryl sulphochlorides, with subsequent isolation of the end product. The process is effected in several steps:

Preparing thiophenolate of heavy metal, reacting it with aryl halides or aryl sulphochlorides in a medium of a polar solvent; extraction of the organic layer, its neutralization, drying, distillation of the solvent, and distillation or re-crystallization of the end product.

Disadvantages inherent in the known methods are complexity of the process (arrangement of the process in several steps, high labour consumption) and difficulty of carrying it out on an industrial scale.

The object of the invention is to simplify the process and to make it operable on an industrial scale.

This object has been accomplished in that a method of preparing symmetrical diarylsulphides, has been provided in which, according to the invention vention an aromatic thiol is passed through an atmosphere of a gas inert to said thiol, at a temperature of 500°–600° C with subsequent isolation of the end diarylaslphide product.

It is recommended that nitrogen be used as the inert gas.

The herein-proposed method of preparing symmetrical diarylsulphides is based on the reaction of condensation of aromatic thiols at a temperature of 500°–600° C in an atmosphere of a gas inert to the thiols. The reaction proceeds according to the following scheme:

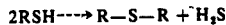

where R is aryl.

The starting thiols, for example, thiophenol, 4-thiocresol or 1-thionaphthol are passed through an empty silica tube at a temperature of 500°–600° C in an atmosphere of an inert gas (preferably nitrogen).

The yield of diarylsulphides is to 60 per cent by weight.

The present invention is much simpler to carry out than the prior art processes in that it is effected in a single step only, it utilizes simpler equipment, the end product is isolated by a simple technique, and finally, it can be carried out on an industrial scale.

For a better understanding of the invention, the following examples of its practical embodiment are given by way of illustration.

EXAMPLE 1

Thiophenol (6.1 g or 0.05 mole) is passed through a 655-mm long silica tube having the diameter of 30 mm and heated to a temperature of 560° C, at a rate of 10 ml/hr together with nitrogen which is passed at a rate of 5 liter/hr. The contact time is 35 seconds. The condensate is collected in a cooled receptacle. The condensate is fractionated in vacuum to give 2.0 g (48 per cent by weight, calculated with reference to the reacted thiophenol) of diphenylsulphide boiling at 118°–121° C (4 mm Hg), $n_D20$ 1.6312 and 0.5 of the starting thiophenol.

EXAMPLE 2

The procedure is the same as described in Example 1, except that the starting substance is 4-thiocresol, taken in a quantity of 5.0 g (0.045 mole), and the process temperature is 580° C. The yield is 2.0 g (61 per cent by weight, calculated with reference to the reacted 4-thiocresol) of di(4-tolyl) sulphide melting at 56.5° C (from ethyl alcohol) and 1.2 g of the starting 4-thiocresol.

EXAMPLE 3

The procedures is the same as described in Example 1 except that the starting substance is 1-thionaphthol, taken in the quantity of 0.04 mole or 5.0 grams, and the process temperature is 530° C. The yield is 2.5 g (55.8 per cent by weight, calculated with reference to the reacted 1-thionaphthol) of di(1-naphthyl) sulphide, melting at a temperature of 105°–107° C, and 0.5 g of 1-thionaphthol.

What we claim is:

1. A method of preparing a symmetrical diarylsulphide which consists of passing an aromatic thiol through a reaction zone, heating said reaction zone in the absence of a catalyst to a temperature of about from 500° C to 600° C to convert said thiol into a symmetrical diarylsulphide, and isolating said diarylsulphide.

2. The method of claim 1 wherein the gas is nitrogen.

3. The method of claim 1 wherein the aromatic thiol is thiophenol, the gas is nitrogen, the temperature is about 560° C, and the diarylsulphide produced is diphenylsulphide.

4. The method of claim 1 wherein the aromatic thiol is 4-thiocresol, the gas is nitrogen, the temperature is about 580° C, and the diarylsulphide produced is di(4-tolyl) sulphide.

5. The method of claim 1 wherein the aromatic thiol is 1-thionaphthol, the gas is nitrogen, the temperature is about 530° C and the diarylsulphide produced is di(1-naphthyl) sulphide.

6. A method of preparing a symmetrical diarylsulphide which consists of pyrolyzing an aromatic thiol in an atmosphere of a gas inert to said thiol, at a temperature of about from 500° C to 600° C, to produce a symmetrical diarylsulphide, and isolating said diarylsulphide.

7. The method of claim 6 wherein the gas is nitrogen.

* * * * *